United States Patent [19]

Komatsu et al.

[11] Patent Number: 5,422,925

[45] Date of Patent: Jun. 6, 1995

[54] CONTAMINATING-ELEMENT ANALYZING METHOD AND APPARATUS OF THE SAME

[75] Inventors: Fumio Komatsu, Fuchu; Kunihiro Miyazaki, Nerima; Ayako Shimazaki, Yokohama, all of Japan

[73] Assignee: Kabushiki Kaisha Toshiba, Kawasaki, Japan

[21] Appl. No.: 116,750

[22] Filed: Sep. 7, 1993

[30] Foreign Application Priority Data

Sep. 7, 1992 [JP] Japan ............................ 4-238535

[51] Int. Cl.⁶ ........................................ G01N 23/223
[52] U.S. Cl. ........................................ 378/45; 378/44
[58] Field of Search ............................ 378/44, 45

[56] References Cited

U.S. PATENT DOCUMENTS

| 4,188 | 1/1897 | Thomson et al. | 378/45 |
|---|---|---|---|
| 3,764,805 | 10/1973 | Alley | 378/48 |
| 4,009,390 | 2/1977 | Sutterlee et al. | 378/45 |
| 4,015,124 | 3/1977 | Page | 378/45 |
| 5,365,563 | 11/1994 | Kira et al. | 378/48 |

*Primary Examiner*—Paul M. Dzierzynski
*Assistant Examiner*—David Vernon Bruce
*Attorney, Agent, or Firm*—Foley & Lardner

[57] ABSTRACT

A contaminating-element analyzing method and an apparatus of the same are disclosed. Differential smoothing process is performed for a measured waveform of a fluorescent X-ray obtained from an object to be measured so as to detect a peak of the measured waveform, the object containing a contaminating element. A model function with variables which are initial parameters with respect to each peak of the measured waveform is provided so as to constitute a model waveform. A nonlinear optimizing process is performed using the method of least squares of the model waveform and the measured waveform so as to decide initial parameters of each model function and to obtain discriminated waveforms. A contaminating element is identified corresponding to each of the discriminated waveforms and obtaining an integrated intensity of a discrete waveform of each of the identified contaminating elements. A background intensity is obtained corresponding to a measured waveform of a fluorescent X-ray obtained from a non-contaminating object which does not contain any contaminating element. The background intensity is subtracted from an integrated intensity of a discrete waveform of each contaminating element.

9 Claims, 3 Drawing Sheets

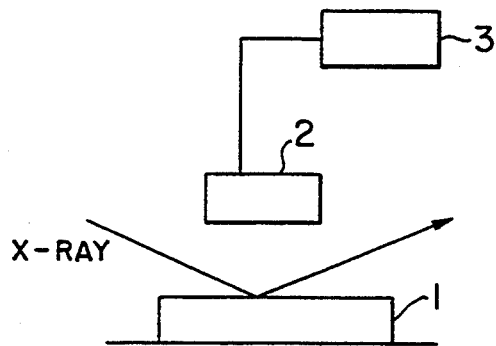
FIG. 2
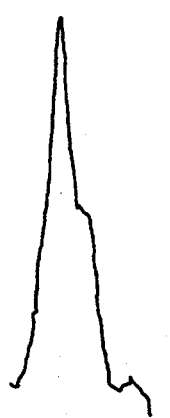
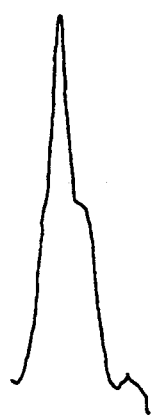
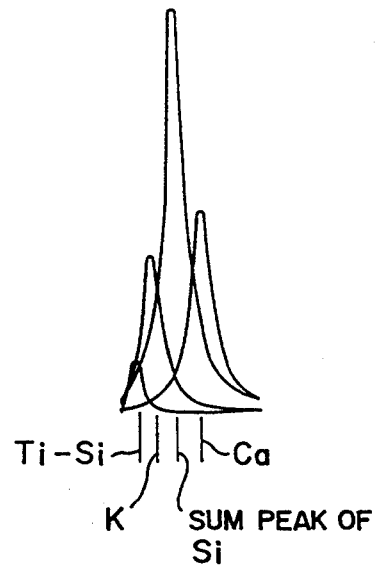
FIG. 3(a)　　FIG. 3(b)　　FIG. 3(c)

CONTAMINATING-ELEMENT ANALYZING METHOD AND APPARATUS OF THE SAME

BACKGROUND OF THE INVENTION

1. Field of the Invention

The present invention relates to a contaminating-element analyzing method using a total reflection X-ray fluorescence analysis and an apparatus of the same, in particular, to a contaminating-element analyzing method for allowing contaminating elements to be detected and the concentrations thereof to be precisely calculated and an apparatus of the same.

2. Description of the Related Art

Thus far, as a method for nondestructively analyzing elements contained in samples, a fluorescent X-ray have been used. In addition, to improve the sensitivity of the analysis, total reflection X-ray fluorescence analyzing methods have been developed. The application of this method to contamination control for semiconductor production lines are being studied.

Among the total-reflection X-ray fluorescence analyzing methods, since energy dispersive-type fluorescent X-ray analyzing method allows a spectrum of a wide energy region to be measured, multi elements can be measured simultaneously with a single solid-state detector (SSD) disposed just above a sample. In addition, since the energy dispersive-type fluorescent X-ray analyzing method does not require a crystal monochromator, the SSD can be disposed at a position very close to a sample. Thus, the energy dispersive-type fluorescent X-ray analyzing method can provide higher sensitivity than for example wave dispersive-type fluorescent X-ray analyzing method.

In the conventional energy dispersive-type fluorescent X-ray analyzing method, if the concentration of a contaminating-element is high (for example, around $10^{11}$ atoms/cm$^2$), the peak and escape peak of the element can be easily identified in the measured waveform of the fluorescent X-ray. An integrated intensity for obtaining the concentration of an element can be calculated with a low error.

However, when a contaminating-element in the level ranging from $10^8$ to $10^9$ atoms/cm$^2$ which is required in the semiconductor production lines is quantified by the energy dispersive-type fluorescent X-ray analyzing method, the following problems will take place.

(1) Since the total count number is small, if the concentration of a contaminating element is low, the peak of the element in the measured waveform of a fluorescent X-ray disappears in the background. Thus, the identification of the peak of the element becomes very difficult.

(2) Even if the peak of an element can be identified, it may be difficult to separate this peak from the escape peak of the element. Thus, when the integrated intensity is calculated, an error may take place. In addition, since the escape peak of an element also depends on the intensity of primary X-ray, the amount of contamination, and so forth, it is difficult to quantify the escape peak and feedback it.

(3) In the semiconductor production lines, if a sample is Si substrate, it is difficult to identify the peaks of elements (such as Mg and Al) whose atomic numbers are close to the atomic number of Si regardless of the concentrations of their contaminations. In addition, sum peaks which are present at peak positions of $n \times$Si—K$\alpha$ (where n is any integer) become interfering peaks.

(4) To raise the sensitivity of analysis, an Primary X-ray which is provided with a rotating target is used so as to increase the output power. In this case, since the effect of Compton scattering of a primary X-ray is large, the peak of an element may disappear in the spectrum of the primary X-ray. For example, in W-L$\beta_1$ of a Primary X-ray, which has a high excitation efficiency against a transition metal, the identification of the peak of Zn may be difficult.

The present invention is made from the abovedescribed point of view.

SUMMARY OF THE INVENTION

An object of the present invention is to provide a contaminating-element analyzing method using a fluorescent X-ray and an apparatus of the same, in particular, to a contaminating-element analyzing method for allowing contaminating elements to be detected and the concentrations thereof to be precisely calculated and an apparatus of the same.

A first aspect of the present invention is a contaminating-element analyzing method, comprising the steps of performing a differential smoothing process for a measured waveform of a fluorescent X-ray obtained from an object containing contaminating elements to be measured so as to detect peaks of said measured waveform, providing a model function with variables which are initial parameters with respect to each peak of said measured waveform and linearly summing the model functions so as to constitute a model waveform, performing a nonlinear optimization process using the method of least squares of said model waveform and said measured waveform so as to decide initial parameters of each model function and to obtain discriminated waveforms, and identifying a contaminating element corresponding to each of said discrimianted waveforms and obtaining an integrated intensity of the discrete waveform of each of the identified contaminating elements.

A second aspect of the present invention is a contaminating-element analyzing apparatus, comprising means for performing differential smoothing process for a measured waveform of a fluorescent X-ray obtained from an object containing contaminating elements to be measured so as to detect peaks of said measured waveform, means for providing a model function with variables which are initial parameters with respect to the peak of said measured waveform and linearly summing the model function so as to constitute a model waveform, means for performing a nonlinear optimization process using the method of least squares of said model waveform and said measured waveform so as to decide initial parameters of each model function and to obtain discrimianted waveforms, and means for identifying a contaminating element corresponding to each of said discrimianted waveforms and obtaining an integrated intensity of the discrete waveform of each of the identified contaminating elements.

According to the present invention, with discrimianted waveforms obtained by the nonlinear optimization process, contaminating-elements can be easily identified. In addition, by subtracting the background intensity from the integrated intensity of each contaminating element, the concentration thereof can be precisely obtained.

These and other objects, features and advantages of the present invention will become more apparent in light of the following detailed description of a best mode embodiment thereof, as illustrated in the accompanying drawings.

BRIEF DESCRIPTION OF DRAWINGS

FIG. 2 is a schematic diagram showing an energy dispersive-type fluorescent X-ray analyzing apparatus;

FIG. 3(a) is a schematic diagram showing a measured waveform according to the embodiment of the present invention;

FIG. 3(b) is a schematic diagram showing a smothed waveform according to the embodiment of the present invention;

FIG. 3(c) is a schematic diagram showing discriminated waveforms according to the embodiment of the present invention;

DESCRIPTION OF PREFERRED EMBODIMENTS

Figure 1:
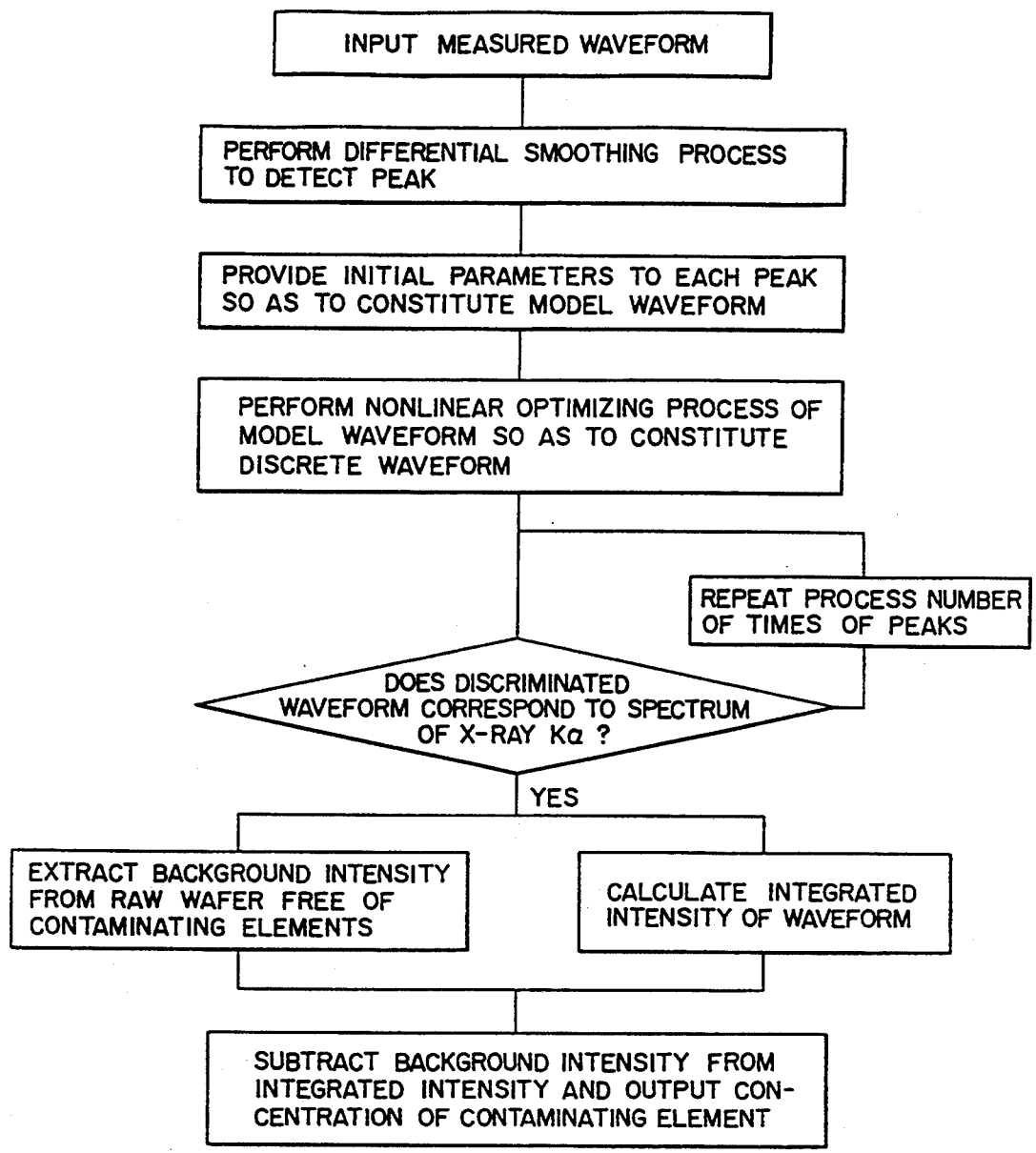
FIG. 1 is a flow chart showing a contaminating-element analyzing method according to an embodiment of the present invention.

With reference to the accompanying drawings, an embodiment of the present invention will be described.

FIGS. 1 to 5 are schematic diagrams showing a contaminating-element analyzing method and an apparatus of the same according to an embodiment of the present invention.

With reference to FIG. 2, an energy dispersive-type fluorescent X-ray analyzing apparatus will be described in brief. In the figure, reference numeral 1 depicts a sample (an object to be measured) which is for example a Si wafer. The sample 1 is irradiated with an primary X-ray. Thus, a fluorescent X-ray is emitted from the sample 1. The fluorescent X-ray is detected by a solid-state detector 2 (SSD). The SSD 2 is connected to a signal processing device 3. The signal processing device 3 receives an electric signal from the SSD 2 and processes the signal.

Next, with reference to FIGS. 1 and 2, a contaminating-element analyzing method and a contaminating-element analyzing apparatus both of which use the energy dispersive-type fluorescent X-ray analyzing apparatus will be described.

An X-ray is irradiated to the sample 1 containing an contaminating-element. Thus, the sample 1 gives off a fluorescent X-ray. The fluorescent X-ray is detected by the solid-state detector (SSD) 2. The waveform measured by the SSD 2 is transferred to the signal processing device 3.

The signal processing device 3 processes the measured waveform of the fluorescent X-ray in the following manner. As shown in FIG. 1, differential smoothing process is performed for the measured waveform over five adjacent channels thereof (the reason the five channels are selected is typical SSD linewith and energy resolutions vary channel from channel). Thereafter, corresponding to the integrated waveform, a zero cross points are detected as a candidacy of the peak of the measured waveform.

Next, a model function (for example, Gauss' function) is provided for each peak of the measured waveform. By linearly summing each Gauss' function, a model waveform is constituted. In this case, each Gauss' function has initial parameters which are peak position (u), peak height (h), and half width of half maximum (w). These initial parameters are variables of each Gauss' function. Thus, there is the following relation.

$$z(i, p) = \Sigma_j h \cdot \exp\{-\ln 2(v-u)^2/w^2\}$$

where j corresponds to each peak being detected.

The peak position (u) of each Gauss' function is approximately defined by a channel number i corresponding to each peak of the measured waveform. The peak height (h) is approximately defined by each peak of the measured waveform. The half width of half maximum (w) is approximately defined by a point where a ternary differentiated value of each Gauss' function becomes 0.

Next, a nonlinear optimization process using the method of least squares of the model waveform and the measured waveform is performed so as to decide the above-described initial parameters and to obtain the discrete waveform of each Gauss' function. In other words, the differential square sum of the model waveform z (i, p) and the measured waveform y (i) is defined as an objective function e (p) as follows.

$$e(p) = \Sigma\{z(i, p) - y(i)\}^2$$

where $z(i, p) = \Sigma_j h \cdot \exp\{-\ln 2(v-u)^2/w^2\}$, and j corresponds to each peak being detected.

A vector variable p where the objective function e (p) becomes minimum is obtained by using the nonlinear optimization method based on a simplex method. It should be noted that instead of the simplex method another appropriate method may be used.

Next, the peak position of the discrete waveform and the peak position of kα X-ray of each element are compared on the basis of the discrete waveform of each Gauss' function (obtained by the nonlinear optimizing process). At this point, in consideration of a chemical shift, a predetermined margin is applied. When a Gauss' function corresponding to kα X-ray of an element is found, this Gauss' function is designated as that corresponding to a contaminating element. Peaks which do not correspond to elements are designated as escape peaks, sum peaks, and/or background noises. Then, the integrated intensity (area) of the Gauss' function corresponding to each element is obtained. In this case, each Gauss' function is integrated in the range of ±4α (where α is the standard deviation of the Gauss' function).

The integrated intensity of Gauss' function corresponding to each element contains a background. To remove the effect of the background, the background intensity is obtained from a raw semiconductor wafer which does not contain any contaminating-elements (namely, the the raw Si wafer) corresponding to the measured waveform of a fluorescent X-ray. The resultant value is stored as a table. Next, from the table, the background intensity is extracted. By subtracting the background intensity from the integrated intensity of the Gauss' function corresponding to each element, the concentration of each element can be obtained.

In the above-described embodiment, Gauss' function was used as a model function. However, it should be noted that instead of the Gauss' function, Lorentz's function may be used.

(PRACTICAL EXAMPLE)

Next, with reference to FIGS. 3 to 5, a practical example of the present invention will be described. FIG. 3(a) shows a measured waveform of a fluorescent X-ray. FIG. 3(b) shows a smoothed waveform which is smoothed at five adjacent points of the measured waveform. FIG. 3(c) shows discrimianted waveforms which have been nonlinearly optimized. In FIGS. 3(a) to 3(c), the horizontal axis of each waveform corresponds to energy region whose magnitude is in the range from 2.81 to 3.92 keV.

In FIG. 3 (a), since the interference of the sum peak of Si-kα in the measured waveform is large, the peak of a contaminating element is indefinite. Thus, only with the measured waveform, the integrated intensity cannot be calculated. In contrast, with the discrimianted waveforms shown in FIG. 3(c), Ti escape (Ti—Si), K-kα (k), Si-kα sum-peak (Si sum peak), and Ca-kα (Ca) peak can be clearly identified. In particular, as shown by an arrow of FIG. 3(c), the peak of K atom can be clearly identified.

The Ti escape is a peak which appears in the following manner. If Ti as a contaminating element is contained in a semiconductor wafer made of Si which is a sample, when an X-ray is irradiated to the semiconductor wafer, it gives off a fluorescent X-ray of Ti. Thus, the fluorescent X-ray of Ti reaches a solid-state detector (SSD). Since the SSD is generally Lithium-drifted silicon diode, when the fluorescent X-ray of Ti is irradiated to the SSD, it may give off a fluorescent X-ray of Si. Thus, the SSD detects the difference between energy of Si and energy of Ti. The difference becomes the Ti escape. The Si sum peak is a peak at positions of n×kα X-ray peak position of Si atom (where n is any integer).

Figure 4:
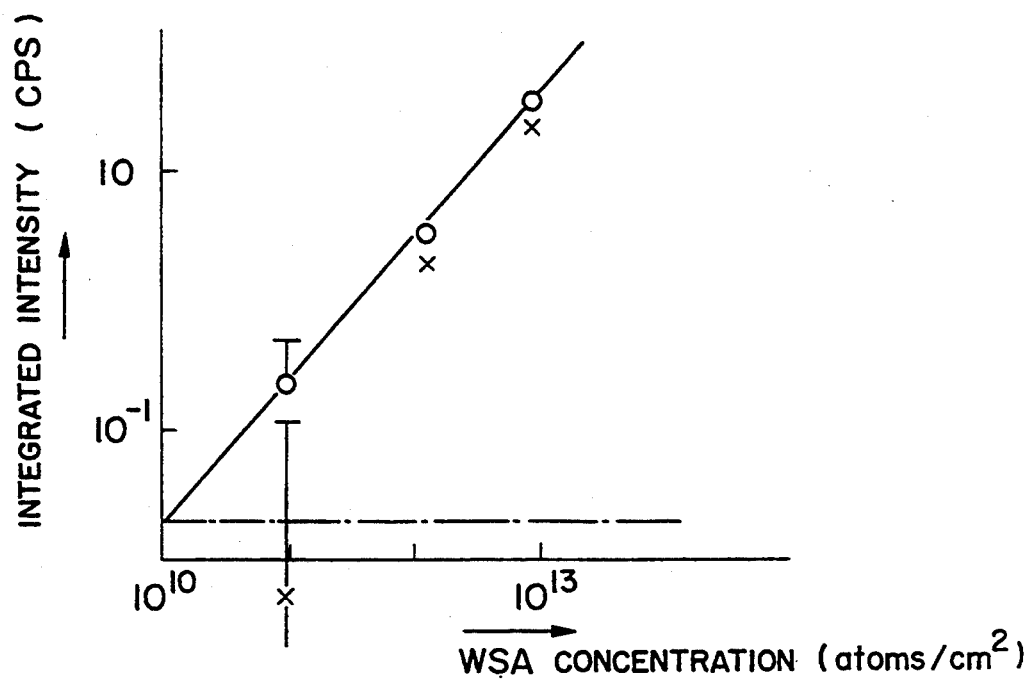
FIG. 4 is a graph showing comparison of a calibration curve of K atom between the present invention and a conventional method.

Next, with reference to FIG. 4, the concentration of K atom obtained by the method according to the present invention and that obtained by the conventional method will be compared. As shown in FIG. 4, in the method according to the present invention (represented by mark o), the integrated intensity and concentration of each element appropriately match each other and thereby a good measured line is obtained. In the conventional method (represented by mark x), however, as the concentration becomes low, the integrated intensity largely deviates against the concentration of an element and thereby their relation cannot be easily quantified.

Figure 5A:
FIG. 5(a) is a schematic diagram showing a measured waveform where Zn atom disappears in the peak of an primary X-ray.
Figure 5B:
FIG. 5(b) is a schematic diagram showing a waveform smoothed at five positions.
Figure 5C:
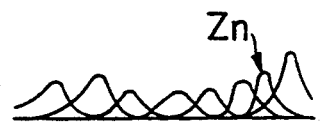
FIG. 5(c) is a schematic diagram showing discriminated waveforms which have been non linearly optimized.

Next, with reference to FIG. 5, the result of peak separation in the case where the peak of Zn atom disappears in a W-Lβ₁ peak of the Primary X-ray is shown. FIG. 5(a) shows a measured waveform where Zn atom disappears in the W-Lβ₁ peak of the primary X-ray. FIG.5 (b) shows a waveform smoothed at five positions. FIG. 5 (c) shows discrimianted waveforms which have been nonlinearly optimized. As shown by an arrow of FIG. 5(c), the peak of Zn atom which was difficult to identify by the conventional method can be clearly identified.

According to the above-described embodiment, even in a low concentration region where interfering peaks cannot be easily discriminated, the concentration of each contaminating element can be precisely obtained without a deviation. In addition, even if the peak of a contaminating element disappear due to Compton scattering, the contaminating element can be clearly identified. Moreover, a contaminating element in the vicinity of the peak of Si-kα can be securely analyzed.

As described above, according to the present invention, contaminating elements can be easily and securely identified. In addition, the concentration of each contaminating element can be accurately obtained.

Although the present invention has been shown and described with respect to a best mode embodiment thereof, it should be understood by those skilled in the art that the foregoing and various other changes, omissions, and additions in the form and detail thereof may be made therein without departing from the spirit and scope of the present invention.

What is claimed is:

1. A contaminating-element analyzing method, comprising the steps of:

performing a differential smoothing process for a measured waveform of a fluorescent X-ray obtained from an object containing contamination elements to be measured so as to detect peaks of said measured waveform, providing a model function with variables which are initial parameters with respect to each peak of said measured waveform and linearly summing the model functions so as to constitute a model waveform;

performing a nonlinear optimization process using the method of least squares of said model waveform and said measured waveform so as to decide initial parameters of each model function and to obtain discriminated waveforms; and identifying a contaminating element corresponding to each of said discriminated waveforms and obtaining an integrated intensity of the discrete waveform of each of the identified contaminating elements.

2. The contaminating-element analyzing method as set forth in claim 1, further comprising the step of:

obtaining a background intensity corresponding to a measured waveform of a fluorescent X-ray obtained from any non-contaminating object which does not contain any contaminating element and subtracting said background intensity from the integrated intensity of the discrete waveform of each contaminating element.

3. The contaminating-element analyzing method as set forth in claim 1, wherein the providing a model function and linearly summing step comprises providing a Gauss' function as said model function and linearly summing the Gauss' function so as to constitute the model waveform.

4. The contaminating-element analyzing method as set forth in claim 3, wherein the identifying and obtaining step comprises integrating said Gauss' function within ±4× a half-width Gauss' function.

5. The contaminating-element analyzing method as set forth in claim 1, wherein the performing a nonlinear optimization process step comprises a simplex method as said nonlinear optimizing process.

6. The contaminating-element analyzing method as set forth in claim 1, wherein the identifying and obtaining step comprises comparing an energy position of each discrete waveform and a peak position of kα X-ray of each element in succession so as to identify the contaminating element.

7. The contaminating-element analyzing method as set forth in claim 6, wherein the identifying and obtaining step comprises comparing an energy position of each discrete waveform and a peak position of kα X-ray of each element with a predetermined margin.

8. A contaminating-element analyzing apparatus, comprising:

means for performing differential smoothing process for a measured waveform of a fluorescent X-ray obtained from an object containing contaminating elements to be measured so as to detect peaks of said measured waveform;

means for providing a model function with variables which are initial parameters with respect to each peak of said measured waveform and linearly summing the model functions so as to constitute a model waveform;

means for performing a nonlinear optimization process using the method of least squares of said model waveform and said measured waveform so as to decide initial parameters of each model function and to obtain discriminated waveforms; and means for identifying a contaminating element corresponding to each of said discriminated waveforms and obtaining an integrated intensity of the discrete waveform of each of the identified contaminating elements.

9. The contaminating-element analyzing apparatus as set forth in claim 1, further comprising:

means for obtaining a background intensity corresponding to a measured waveform of a fluorescent X-ray obtained from a non-contaminating object which does not contain any contaminating element and subtracting said background intensity from the integrated intensity of the discrete waveform of each contaminating element.

* * * * *